United States Patent
Varghese et al.

(10) Patent No.: US 8,328,726 B2
(45) Date of Patent: Dec. 11, 2012

(54) METHOD AND APPARATUS FOR MONITORING TISSUE ABLATION

(76) Inventors: Tomy Varghese, Madison, WI (US); Shyam Bharat, Madison, WI (US)

( * ) Notice: Subject to any disclaimer, the term of this patent is extended or adjusted under 35 U.S.C. 154(b) by 746 days.

(21) Appl. No.: 12/416,485

(22) Filed: Apr. 1, 2009

(65) Prior Publication Data

US 2010/0256530 A1 Oct. 7, 2010

(51) Int. Cl.
*A61B 8/14* (2006.01)
*A61B 8/00* (2006.01)
*A61B 5/103* (2006.01)
*A61B 5/117* (2006.01)
*A61B 18/04* (2006.01)

(52) U.S. Cl. .......... 600/471; 600/438; 600/587; 606/27

(58) Field of Classification Search .................. 600/587, 600/595, 438–439, 471, 466; 606/27–31
See application file for complete search history.

(56) References Cited

U.S. PATENT DOCUMENTS

| 6,575,969 | B1 * | 6/2003 | Rittman et al. ................ 606/41 |
| 7,166,075 | B2 | 1/2007 | Varghese et al. |
| 7,275,439 | B2 | 10/2007 | Zagzebski et al. |
| 7,297,116 | B2 | 11/2007 | Varghese et al. |
| 7,331,926 | B2 | 2/2008 | Varghese et al. |
| 8,150,128 | B2 * | 4/2012 | Konofagou et al. ......... 382/131 |
| 2004/0210135 | A1 * | 10/2004 | Hynynen et al. ............. 600/439 |
| 2005/0277835 | A1 * | 12/2005 | Angelsen et al. ............. 600/437 |
| 2007/0276245 | A1 * | 11/2007 | Konofagou .................... 600/443 |
| 2009/0056453 | A1 * | 3/2009 | McAleavey .................... 73/597 |
| 2012/0158323 | A1 * | 6/2012 | Hazard et al. ................... 702/56 |

* cited by examiner

*Primary Examiner* — Max Hindenburg
*Assistant Examiner* — Adam Eiseman

(57) ABSTRACT

Real-time monitoring of tissue ablation is possible by using a vibrating ablation needle coupling lateral shear waves to the tissue. Ultrasonic imaging may characterize the velocity of these shear waves to reveal Young's modulus of the tissue and, at a discontinuity in Young's modulus, a boundary of the ablated lesion reflecting an underlying increase in stiffness of ablated tissue. This technique may be coupled with quasi-static elastography-based ablation monitoring techniques for improved measurement.

16 Claims, 4 Drawing Sheets

US 8,328,726 B2

METHOD AND APPARATUS FOR MONITORING TISSUE ABLATION

STATEMENT REGARDING FEDERALLY SPONSORED RESEARCH

This invention was made with United States government support awarded by the following agencies:
NIH CA112192
The United States government has certain rights in this invention.

CROSS-REFERENCE TO RELATED APPLICATIONS

BACKGROUND OF THE INVENTION

The present invention relates to radiofrequency or microwave ablation and in particular to a method of monitoring tissue ablation concurrent with the ablation process.

Elastography is an imaging modality that reveals the stiffness properties of tissues, for example, axial strain, lateral strain, Poisson's Ratio, Young's Modulus, or other common stiffness measurements. The stiffness measurements may be output as quantitative values or mapped to a gray or color scale to form a picture over a plane or within a volume.

Generally, stiffness is deduced by monitoring tissue movement under an applied force or deformation. The monitoring may be done by any medical imaging modality including computed tomography (CT), magnetic resonance imaging (MRI), and ultrasonic imaging. Elastography is analogous to a physician's palpation of tissue in which the physician determines stiffness by pressing the tissue and detecting the amount that the tissue yields under pressure.

In "dynamic" elastography, a low frequency vibration is applied to the tissue and the velocity of the resulting compression waves is measured, for example, using ultrasonic Doppler detection. In "quasi-static" elastography, two images of the tissue are obtained at different states of compression, typically using the ultrasonic transducer as a compression paddle. Displacement of the tissue between the two images is used to deduce the stiffness of the tissue.

U.S. Pat. No. 7,166,072, assigned to the same assignee as the present invention and hereby incorporated by reference, describes a novel technique for monitoring a radiofrequency ablation using quasi-static elastography. Radiofrequency or microwave ablation is a process for treating tumors or the like which employs one or more of electrodes inserted percutaneously to the site of a tumor. Ionic heating of the tissue induced by radiofrequency fields in the tissue kills tumor cells and produces a hardened lesion. This lesion, being much stiffer than the surrounding tissue, may be monitored by quasi-static elastography using the ablation electrode as the compression device. Adhesion between the ablated tissue and the electrode allows the source of the compression to be at the site of the tumor (as opposed to external compression to the patient) providing a more accurate characterization of the stress field near the tumor and, accordingly, substantially improved elastographic measurement. As used herein, the term "high-frequency ablation" will be used for ablation using either radiofrequency or microwave frequency electrical energy.

SUMMARY OF THE INVENTION

The present invention provides improved definition of the boundaries of the tumor during ablation, as well as improved quantitative characterization of the tissue by measuring not only axial compression of the tissue but shear wave velocity perpendicular to the deformation axis. A change in velocity of the shear waves characterizes the lateral edges of the ablated volume and provides a direct measurement of Young's modulus of both the ablation volume and surrounding non-ablated tissue. The technique of monitoring axial compression (per U.S. Pat. No. 7,166,075) and the technique of monitoring shear wave velocity can be combined to obtain a more complete and more accurate picture of the ablation volume during ablation, with the axial compression technique providing axial boundaries and the shear wave technique providing lateral boundaries, for example.

Specifically then, the present invention may provide an apparatus for monitoring the progress of radiofrequency ablation having an electrode adapted for percutaneous insertion into tissue at a tumor site and a radiofrequency power source communicating with the electrode to ablate tissue at the tumor site. An actuator communicating with the electrode provides vibration of the electrode along a first axis and a tissue imager measures axial displacement of tissue in a volume extending along a second axis perpendicular to the first axis, such displacement characterizing a shear wave directed along the second axis. An electronic computer receives displacement data from the tissue imager and executes a stored program to:
(a) compute velocity of a shear wave along the second axis;
(b) detect a change in shear wave velocity along the second axis indicating a boundary between ablated and non-ablated tissue along the second axis;
(c) output data indicating a size of an ablation region along the second axis.

It is thus an object of the invention to employ the measurement of shear waves propagated from an ablation electrode to detect the boundary and modulus of an ablation region thereby providing improved guidance to the physician during the ablation process.

The tissue imager may be an ultrasonic imaging device directing an ultrasonic beam along the first axis.

It is another object of the invention to provide improved lateral characterization of ablation volume when using an axially directed ultrasonic probe.

The shear wave velocity may be computed by determining a time of maximum displacement for a variety of points along the second axis and deducing the velocity from the spatial separation of the points divided by differences in the times of maximum displacements for those points.

It is thus an object of the invention to provide a method of determining shear wave velocity using an imaging system.

The electronic computer may further use the velocity of the shear wave to compute the modulus of elasticity of the tissue along the second axis and may characterize the ablated or non-ablated tissue using the modulus of elasticity and wherein the output data indicates this characterization of the ablated or non-ablated tissue.

It is thus an object of the invention to provide an alternative method of measuring tissue elasticity that may be used alone or combined with quasi-static elasticity measurement techniques.

The electronic computer may output quantitative elasticity measurements of the ablated or non-ablated tissue.

It is thus an object of the invention to provide a quantitative elasticity measurement that may be used alone or to calibrate or normalize elasticity measurements made by quasi-static techniques.

The electronic computer may further execute the stored program to measure tissue displacement along the first axis at a first and second time corresponding to different displacements of the electrode by the actuator, and to detect displacement and deduce elasticity along the first axis indicating a boundary between ablated and non-ablated tissue along the first axis. This boundary information may combine the measurement of the boundary between ablated and non-ablated tissue along the second axis to provide output data indicating a multidimensional boundary of an ablated region.

It is thus an object of the invention to better characterize the boundary of the ablation region.

The electronic computer may further execute the stored program to deduce modulus of elasticity of the tissue along the second axis from the velocity of the shear wave and export the modulus of elasticity to regions of the tissue defined by the multidimensional boundary. The measured displacements and modulus of elasticity may be combined, for example iteratively, to provide refined tissue elasticity measurements for the regions.

It is thus an object of the invention to improve quasi-static elasticity measurements.

The electronic computer may further execute the stored program to measure shifts in sound speed deduced from an apparent changing displacement at a predetermined constant vibrational phase of the electrode to estimate tissue temperature during the ablation procedure. The velocity of the shear wave, used to compute modulus of elasticity of the tissue, may be used to correct this deduced temperature.

It is thus an object of the invention to provide more accurate absolute temperature information.

The actuator may provide the vibration through reciprocation of a free mass.

It is thus an object of the invention to permit a handheld probe that may be easily manipulated by the physician for quasi-static compression and vibrated without attachment to a fixed support for shear wave generation.

These particular objects and advantages may apply to only some embodiments falling within the claims, and thus do not define the scope of the invention.

DETAILED DESCRIPTION OF THE PREFERRED EMBODIMENT

Figures 1, 2, 3:
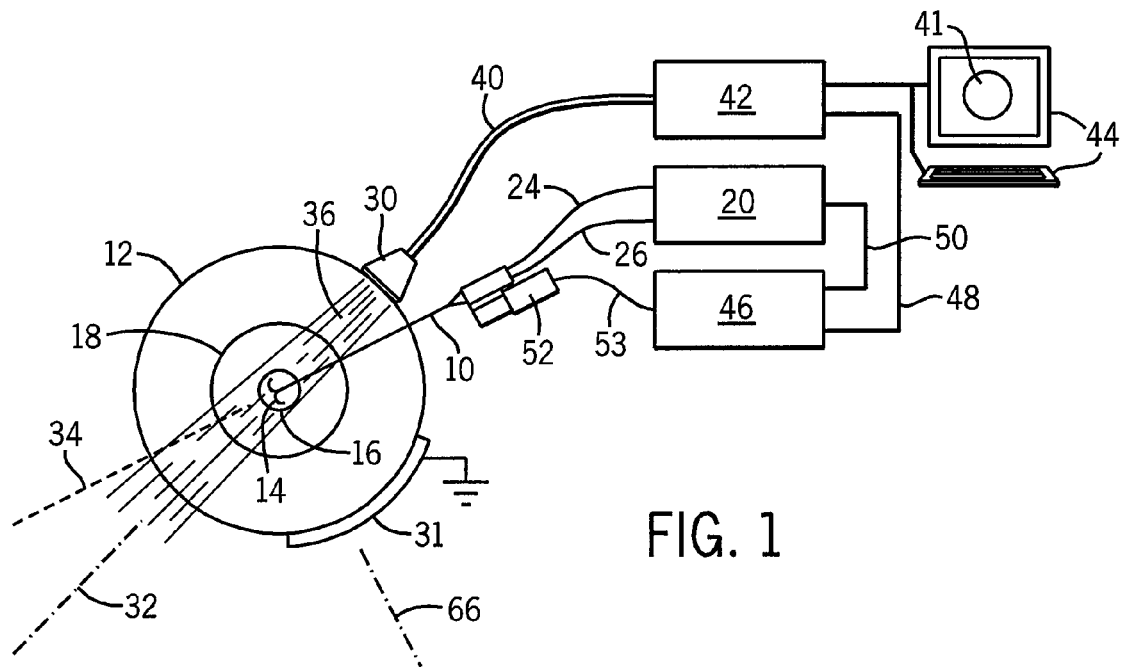
FIG. 1 is a simplified block diagram of an RF ablation system for use with the present invention showing: insertion of an ablation probe into a tumor site of an in vivo organ, an ultrasonic imaging system for imaging of the organ and tumor site, and a control system for applying controlled quasi-static compression and shear wave inducing vibration to the tumor site through the RF ablation probe.
FIG. 2 is a simplified depiction of the tumor of FIG. 1 showing various modes of tissue vibration including an axial compression wave aligned with a vibration axis of the ablation probe and a shear wave traveling along a lateral axis perpendicular to the vibration axis.
FIG. 3 is a simplified plot of quasi-static elasticity versus axial distance showing changes in the elasticity demarcating an ablation volume along the vibration axis according to prior art techniques.

Referring now to FIG. 1, an RF ablation probe 10 may be inserted percutaneously into a patient 12 to have its tip located at an ablation region 16 within an organ 18 such as the liver.

Extensible electrode tines 14, at the tip of the probe 10, may grip the tissue of the ablation region and provide a greater area of electrical contact to conduct ablative current from a radiofrequency (RF) source 20. Electrical energy from the RF source 20 is conducted through an insulated shaft of the probe 10 to the conductive tines 14 where ionic heating of the tissue kills tumor tissue. A large-area grounding pad 31 placed on the patient's skin provides a return path for this current. The tines 14 may include thermocouples for temperature measurements.

RF ablation probes 10 of this kind having extensible tines and thermocouple sensors are well known in the art and readily available. The RF source 20 may be a Rita Model 30 electrosurgical device manufactured by Rita Medical Systems Inc., Mountain View, Calif., or other similar device.

RF ablation probes 10 of this kind may also be a single 17-gauge electrode, with a 2-3 cm long electrically-active region at the tip embedded in tissue. These electrodes offer the option of internally circulating chilled water during the ablation procedure, which prevents the charring of tissue adjacent to the electrically-active region of the electrode. The RF source 20 may also be a Valleylab Cool-tip™ ablation electrode manufactured by Valleylab, Colo., USA., or other similar device.

During the ablation process, electrical current is conducted from the RF source 20 along line 26 to the ablation probe 10. The temperature signal is returned along line 24 to be received by the RF source 20 and used to limit the temperature of ablation according to techniques well understood in the art.

Imaging of the tissue and the tip of the probe 10 may be done using any ultrasonic imaging system, for example, the Siemens Antares Real Time Scanner manufactured by Siemens Incorporated of California. The ultrasonic imaging system in one embodiment includes an ultrasonic transducer 30 and ultrasound processing circuitry 42. The ultrasonic transducer 30 may be, for example, a linear array transducer approximately forty millimeters wide, operating with dynamic focus over a forty percent bandwidth and producing signals at a center frequency of five megahertz. Generally, 1 D, 1.5 D, and 2 D transducers 30 are suitable for the image generation process.

During insertion of the probe 10, the ultrasound transducer 30 is placed against the skin of the patient and moved as needed for accurate visualization of the tip of the probe 10 with respect to the organ 18. Generally, during the elastographic imaging to be described, the axis 32 of the ultrasound transducer 30 (along which the signals 36 propagate) is aligned as closely as possible to the axis 34 along which the probe 10 is inserted and directed to send the ultrasonic signals 36 into the ablation region 16. The probe 10 stabilizes the organ 18 and prevents lateral shifting along axis 66.

During both insertion of the probe 10 and the ablation process, ultrasonic signal 36 travels into the tissue and is reflected at various tissue structures and boundaries. These echoes are detected by the ultrasound transducer 30 and conducted by cable 40 to the ultrasound processing circuitry 42. The received signals are digitized at a sampling rate of approximately 50 megahertz and then processed according to techniques well known in the art, to produce an image, for example, a B-mode image, on display terminal 44. The ultrasonic signal 36 extends generally along a plane incorporating axis 34 and defining an image plane of the B-mode image.

The controller 46, which may be a computer or logic controller programmed as described below, also receives temperature information via the RF source 20 along cable 50. This temperature information may also be used to provide control signals to the RF source 20 from the controller 46 to further control the RF ablation as well as to generate and normalize thermographic images as will be described. Controller 46 also provides output lines 53 connected to a motorized carriage 52, for example, using a motor and a lead screw to provide motion of the probe 10 along its insertion axis 34 in a controlled manner according to signals on output line 53 as will also be described. Other mechanisms for implementing the motorized carriage 52 may be used including those which apply a predetermined compressive force or low frequency oscillation as will be described below. The controller 46 may also communicate with display terminal 44 for displaying images and receiving user input commands.

According to the invention, the digitized echo signals are further processed either within the ultrasound processing circuitry 42 (for example a computer) to produce an elastographic image 41, or within controller 46. In the former case, line 48 communicates signals from the controller 46 to the ultrasound processing circuitry 42 to coordinate generation of the elastographic image; in the latter case line 48 carries the control signals and digitized echo signals from the ultrasound processing circuitry 42 to the controller 46 for processing by the controller 46.

Referring now to FIG. 2, during a first and optionally only measurement period, the probe 10 is vibrated 60 along the axis 34 of the probe 10. This vibration produces compression waves 62 traveling axially upward and downward from the ablation region 16 (only downward waves are shown for clarity) and shear waves 64 traveling laterally left and right along a lateral axis 66 substantially perpendicular to a vibration axis parallel to the axis 34 of the probe 10. As is understood in the art, compression waves 62 involve a dilation and contraction of tissue indicated by arrows 68 along the axis 34 while the shear wave 64 involves a sliding of tissue with respect to neighboring tissue along axis 34 in shear indicated by arrows 70. Generally both waves 62 and 64 propagate outward during vibration of the probe 10 albeit at different speeds.

During this measurement period, the shear waves 64 generated by vibration 60 of the probe 10 are captured by rapid imaging of the tissue at a frequency substantially greater than that of the vibration 60 (or by "snapshot" imaging at evolving phases over many cycles of the vibration 60) to accurately characterize shear motion of the tissue over time. In the preferred embodiment, the vibration 60 of the probe 10 is in a range of 1 to 1000 Hz and preferably in the 1-50 Hz range with an amplitude of a fraction of a millimeter. As the vibration frequency decreases, the time-to-peak displacement increases, necessitating an increased time-duration for analysis.

In the present invention, an optional second measurement period may be made in which quasi-static compression is used to provide at least two different states of tissue compression where the tissue is essentially at rest during the compression state. This quasi-static compression may occur at a frequency substantially less than 1 Hz with an amplitude of several millimeters and, in one embodiment, may be done by hand. In the present invention, the compression waves 62 are not employed.

Figure 5:
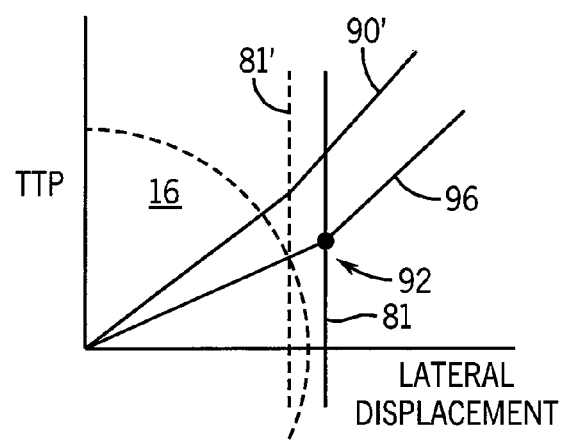
FIG. 5 is a plot of calculated shear wave velocities with respect to lateral distance from the electrode, showing a breakpoint in shear wave velocity demarcating a boundary of the ablated tissue for two different lesions.
Figure 6:
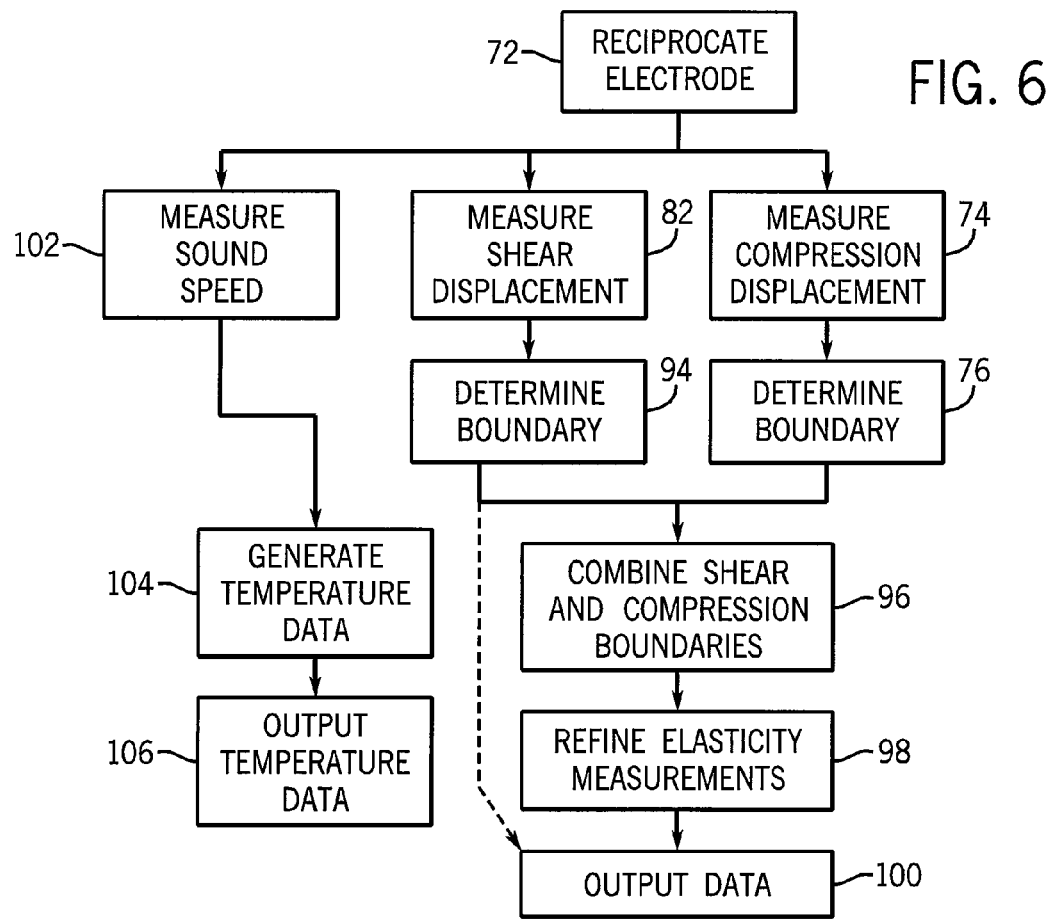
FIG. 6 is a flow chart of a program executed by the control system of FIG. 1 implementing the present invention.

Referring now to FIGS. 3 and 6, the shear wave vibration 60 and the quasi-static compression may be performed at sequential non-overlapping times as indicated by process block 72. At process block 74, axial displacement may be determined from the quasi-static compression, and elasticity of different volume elements about the region 16 may be determined. Referring momentarily to FIG. 2, as has been described in U.S. Pat. No. 7,166,075 incorporated by reference above, this axial displacement may be used to determine tissue elasticity about the ablation region 16 and, in particular, along the axis 34. An analysis of elasticity versus axial distance per process block 76 will show a discontinuity 78 demarcating a boundary 81 between the stiffer ablated tissue of ablation region 16 and the softer unablated tissue 80 along each ray line of the ultrasound signal 36. This approach may be used to define a boundary 81 (shown in FIG. 5 as will be described below) of the ablation region 16 and is particularly accurate for axial boundaries.

Referring to FIGS. 2 and 6, in addition, the displacement of the shear waves 64, may be measured, as indicated by process block 82, and may be used to deduce a shear wave velocity.

Figure 4:
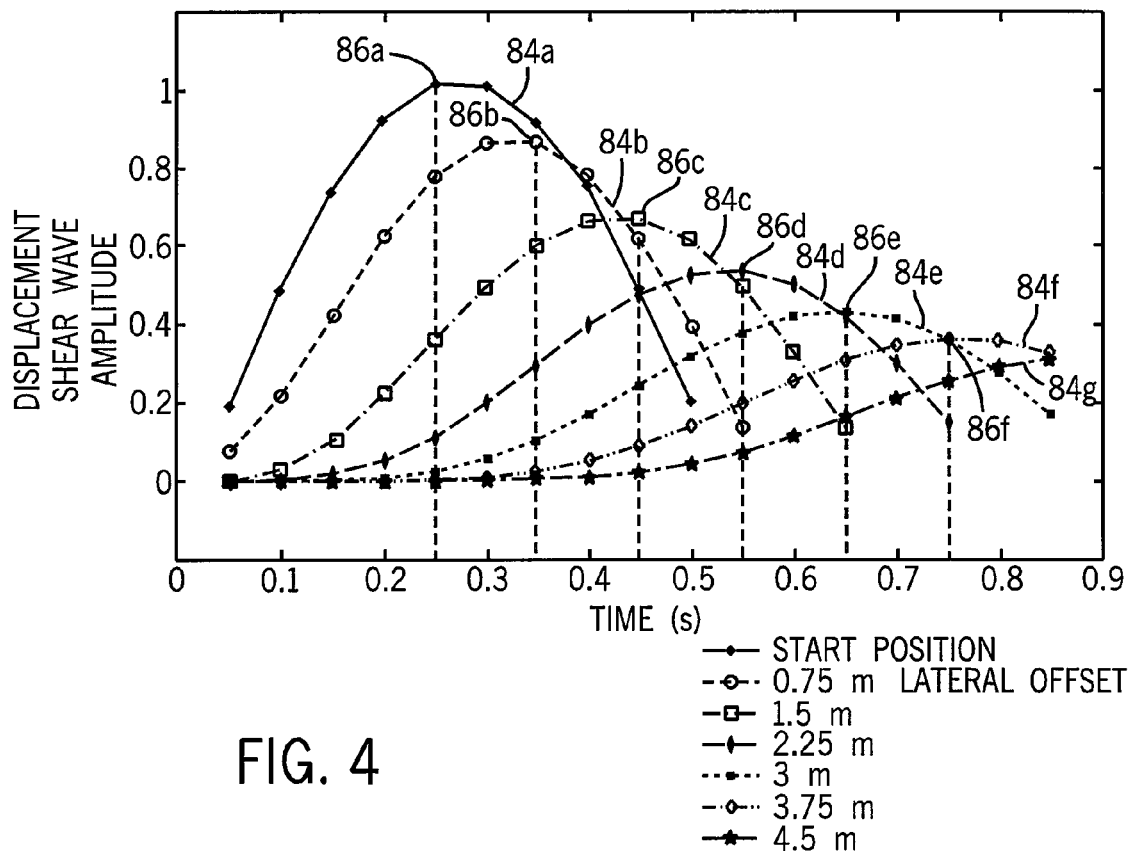
FIG. 4 is a plot of displacement versus time for a set of different laterally separated points, each point associated with a different curve.

Referring now to FIG. 4, this shear wave velocity may be obtained by monitoring series of displacement profiles 84a-g taken at each of a set of laterally displaced points along lateral axis 66. Each displacement profile 84a-g measures time-evolving axial displacement at that point. These displacement profiles 84a-g are analyzed to find the time to peak displacement (TTP) indicated by points 86a-g respectively.

The TTP data indicates the absolute time of passage of a crest of the shear wave across the different points and thus can be used to deduce shear wave velocity. Generally, the shear wave velocity is related to Young's modulus by the following equation:

$$v_s = \sqrt{\frac{E}{3\rho}} \tag{1}$$

(a) where:
(b) $v_s$ is the shear wave velocity;
(c) E is Young's modulus;
(d) and $\rho$ is the material density.

Referring to FIG. 5, a plot 90 of time to peak displacement at each point versus lateral location of the point indicates by its slope the inverse of shear wave velocity. The plot 90 will show a breakpoint 92 at the boundary 81 of the ablation region 16 caused by a transition from stiffer to softer tissue and a resulting change in shear wave velocity. Generally, the ablated tissue within the ablation region 16 will be stiffer as a result of processes such as coagulation.

In addition to defining a boundary 81 of the ablated tissue, the slope of plot 90 will show changes in the absolute stiffness of the ablation region 16 during the ablation process as it evolves, for example, from plot 90' earlier in the ablation process. In this example, plot 90' shows both an earlier boundary 81' and a slightly more elastic ablation region. The ability to extract elasticity data from plots 90 and 90', in addition to the discontinuity data, provides additional insight into the ablation process.

The detection of the boundary 81 of the ablated tissue operates synergistically with the determination of Young's modulus for the regions by allowing data of the regions to be combined for a more robust measurement of Young's modulus in each region. For example, after determination of the boundary 81, Young's modulus may be recalculated separately inside and outside the boundary 81 to provide a more accurate measurement of Young's modulus for these regions. Simulations have suggested that Young's modulus may be accurately determined for the different regions in this fashion per the following Table I.

TABLE I

| Actual Modulus Of Lesion | Measured Modulus Of Lesion | Actual Modulus Of Surrounding Tissue | Measured Modulus Of Surrounding Tissue | Modulus Ratio of Lesion to Surrounding Tissue |
|---|---|---|---|---|
| 10 | 11.317 | 10 | 10.523 | 1:1 |
| 20 | 26.938 | 10 | 10.157 | 2:1 |
| 50 | 57.293 | 10 | 8.314 | 5:1 |
| 100 | 114.19 | 10 | 10.523 | 10:1 |

This process of extracting a breakpoint 92 and thus a boundary of the ablated tissue, and in deducing Young's modulus of the different ablation regions, is represented in FIG. 6 as process block 94.

Referring still to FIG. 6, the shear wave deduced boundary 81 and extraction of Young's modulus from the shear wave may be used alone or may be combined, as indicated by process block 96, with the data collected in quasi-static compression (per process blocks 74 and 76) to provide an improved description of the boundary 81. Generally this combination may use a weighting of boundaries 81 determined at process blocks 76 and 94 where data from process block 94 is given a greater weight for the lateral boundary along lateral axis 66 and the data from process block 76 is given greater weight for the axial boundary along axis 34.

Figure 7:
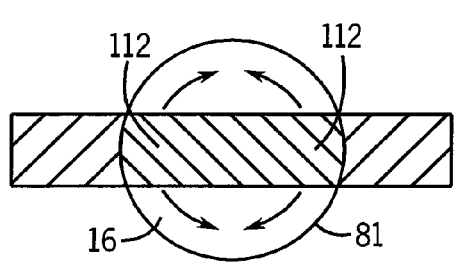
FIG. 7 is a representation of an ablation volume showing regions of known modulus of elasticity that may be mapped to the remainder of the volume per the present invention.
Figure 9:
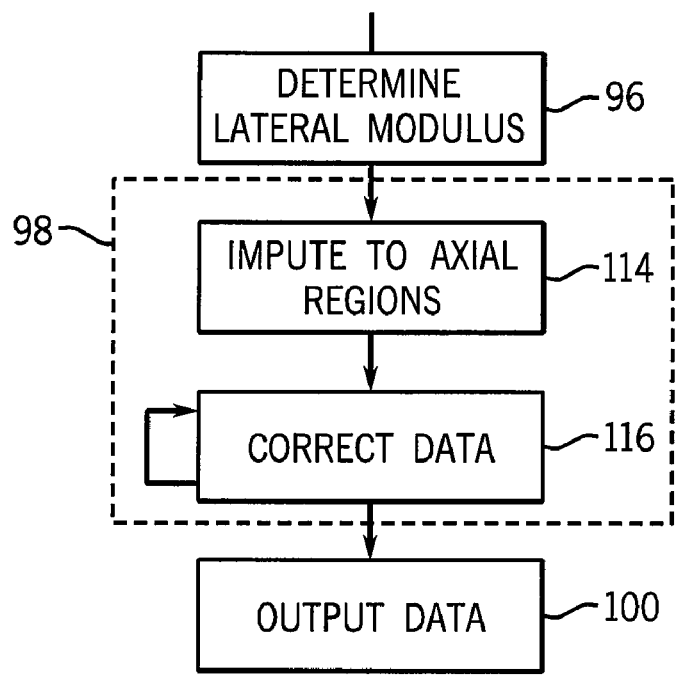
FIG. 9 is a fragmentary flowchart showing use of the modulus of elasticity to refine axial elastographic measurements.

At optional process block 98, the Young's modulus data may be used to refine the elasticity measurements as well as the boundaries themselves. Referring to FIGS. 7 and 9, following the extraction of Young's modulus at process block 96, Young's modulus will be well characterized in lateral bands 112 to the sides of the ablation region 16 as shown in FIG. 7. The data of the bands 112 may be imputed to the remainder of the ablation region 16 within the boundary 81 of ablated tissue of the ablation region 16 and as indicated by process block 114 of FIG. 9.

At process block 116, elasticity measurements using quasi-static elasticity may then be corrected using this elasticity information from Young's modulus so as to conform to the measurement approaches. This correction can occur in a number of ways. First, the modulus information may be used to provide a calibration of the elasticity measurements obtained by quasi-static methods by matching the known Young's modulus data to the elasticity data obtained in the same region. Alternatively, the two elasticity measurements may be averaged together or otherwise combined. In yet another approach, the Young's modulus data may be used to provide a more accurate model of the stress field implicit in the quasi-static elasticity calculation.

Referring still to FIG. 6, data from the process blocks 94, 96, and/or 98 may be output individually or together in graphical form or as quantitative numeric outputs.

Referring again to FIG. 6, during predetermined intervals in the movement of the electrode at process block 72, when the electrode is at a "baseline" position and generally static, sound speed measurements of the tissue may be made at process block 102. Such sound speed measurements may be made by noting apparent tissue displacement from earlier measurements caused by changes in the sound speed through the tissue as described in U.S. Pat. No. 7,166,075 cited above to provide temperature data as indicated by process block 104. This temperature data may be output, as indicated by process block 106, as a numeric output associate with the ablated tissue, for example and average or lowest temperature within the boundary 81, or as an image, for example, a color overlay on top of an image output at process block 100. This data is presented to provide guidance to the physician undertaking the ablation as to the temperature of the tissue and the progress of the ablation and may be further calibrated by temperature sensors on the probe 10 itself. Knowledge of Young's modulus from the shear wave measurements permits more accurate temperature measurements using this process.

Figure 8:
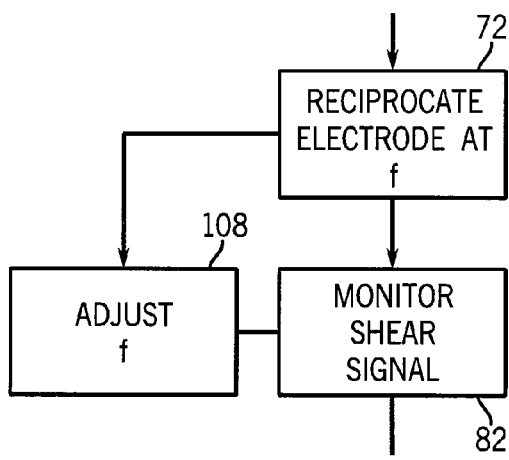
FIG. 8 is a fragmentary flowchart showing additional steps for identifying a vibration frequency dynamically during the ablation process.

Referring now to FIG. 8, process block 72, as described before, may provide for different measurement periods during which the probe 10 is moved in quasi-static compression or shear-wave inducing vibration. The measurement of shear displacement at process block 82 permits a dynamic optimization of the vibration speed through the addition of process block 108. At process block 108, the amplitude of the shear wave 66 from process block 82 may be monitored and based on that monitoring a new vibration frequency may be communicated to process block 72 so as to optimize the frequency for the particular tissue type. Process block 108 may affect, for example, a slight perturbation in frequencies to deduce a frequency at which shear waves are best measured.

Figure 10:
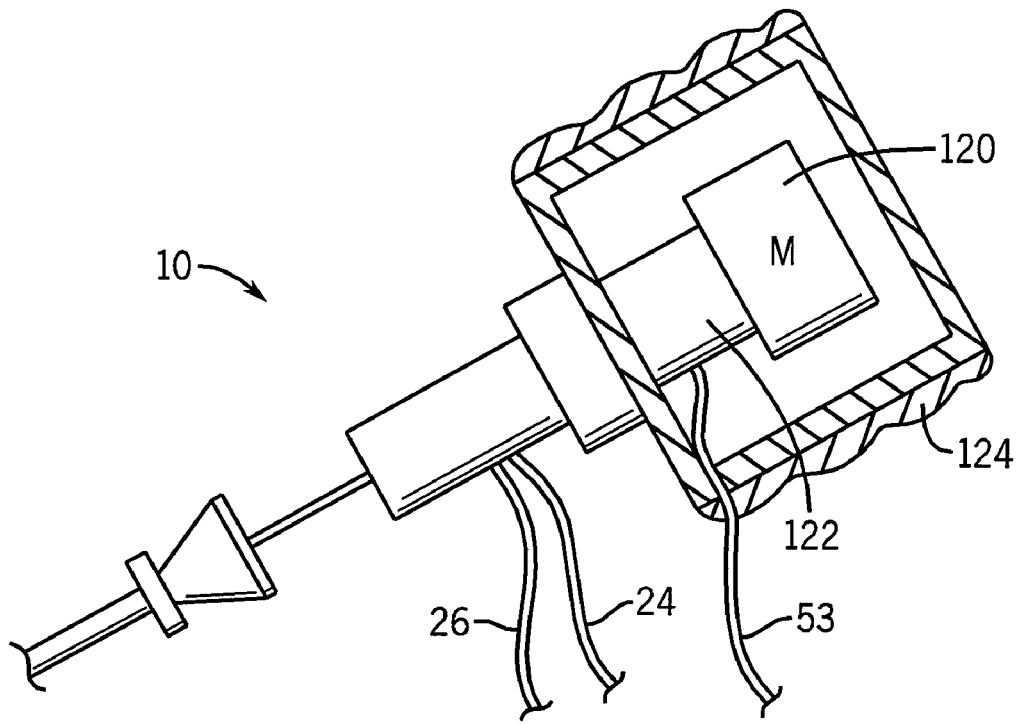
FIG. 10 is a simplified diagram of a hand held electrode providing for desired shear wave generating movement.

Referring now to FIG. 10, in one embodiment of the invention the quasi-static movement of the probe can may be provided manually by the physician and the shear wave induced vibrations may be provided by means of a inertial mass 120 attached to a distal end of the probe 10 via an actuator 122, for example, a solenoid, small motor, or piezoelectric actuator. Activation of the actuator 122 by pulses over lines 53 provides the necessary shear wave inducing movement of the probe 10 and triggers measurement of the peak displacements. Impulse or sinusoidal motions may be readily generated in this manner at a range of desired frequency. A cushioned outer surface 124 may be provided to decouple the vibration from the physician's hand.

It is specifically intended that the present invention not be limited to the embodiments and illustrations contained herein, but include modified forms of those embodiments including portions of the embodiments and combinations of elements of different embodiments as come within the scope of the following claims.

We claim:

1. An apparatus for monitoring progress of high-frequency ablation comprising:
   an electrical probe adapted for percutaneous insertion into tissue to a tumor site;
   a high-frequency power source communicating with the electrical probe to ablate tissue at the tumor site;
   an actuator communicating with the electrode to provide vibration of the electrode along a first axis;
   a tissue imager measuring axial displacement of tissue in a volume extending from the tumor site along a second axis perpendicular to the first axis, such displacement characterizing a shear wave directed along the second axis; and an electronic computer receiving displacement data from the tissue imager and executing a stored program to:
(a) compute a velocity of a shear wave along the second axis;
(b) detect a change in shear wave velocity along the second axis indicating a boundary between ablated and non-ablated tissue along the second axis; and
(c) output data indicating a size of an ablation region along the second axis based on the detected change in shear wave velocity.

2. The apparatus of claim 1 wherein the tissue imager is an ultrasonic imaging device directing an ultrasonic beam along the first axis.

3. The apparatus of claim 1 wherein the shear wave velocity is computed by determining a time of maximum displacement for a variety of points spaced along the second axis and deducing the velocity from a spatial separation of the points divided by differences in the times of maximum displacements for those points.

4. The apparatus of claim 1 wherein the output data is an image.

5. The apparatus of claim 1 wherein the electronic computer further uses the velocity of the shear wave to compute modulus of elasticity of the tissue along the second axis and characterize the ablated or non-ablated tissue using the modulus of elasticity and wherein the output data indicates this characterization of the ablated or non-ablated tissue.

6. The apparatus of claim 5 wherein the electronic computer outputs quantitative elasticity measurements of the ablated or non-ablated tissue.

7. The apparatus of claim 6 wherein the electronic computer outputs image data indicating modulus of elasticity.

8. The apparatus of claim 1 wherein the electronic computer further executes the stored program to:
(d) measure tissue displacement along the first axis at a first and second time corresponding to different displacements of the electrical probe by the actuator;
(e) detect displacement to deduce elasticity along the first axis indicating a boundary between ablated and non-ablated tissue along the first axis;
(f) combine the boundary between ablated and non-ablated tissue along the second axis and the measurement of the boundary between the ablated and non-ablated tissue along the first axis to provide output data indicating a multidimensional boundary of an ablated region.

9. The apparatus of claim 8 wherein the electronic computer further executes the stored program to:
(g) deduce modulus of elasticity of the tissue along the second axis from the velocity of the shear wave;
(h) impute the modulus of elasticity to regions of the tissue defined by the multidimensional boundary;
(i) combine the measured displacements and modulus of elasticity to provide refined tissue elasticity measurements for the regions;
(j) output the elasticity measurements as one of an image or numerical output.

10. The apparatus of claim 9 wherein the combining of the measured displacements and modulus of elasticity use the data to generate a stress field that may be combined with the measured displacements to provide elasticity data.

11. The apparatus of claim 1 wherein the electronic computer executes the stored program to further:
(d) measure shifts in sound speed and tissue expansion deduced from an apparent changing of displacements at a predetermined constant vibrational phase of the electrical probe to estimate a tissue temperature.

12. The apparatus of claim 11 wherein the electronic computer further uses the velocity of the shear wave to compute modulus of elasticity of the tissue, and wherein the tissue temperature is modified by the computed modulus of elasticity of the tissue.

13. The apparatus of claim 1 wherein the vibration has an amplitude of less than 5 mm.

14. The apparatus of claim 1 wherein the vibration has a frequency from one to 1000 Hz.

15. The apparatus of claim 1 wherein the actuator provides the vibration through reciprocation of a free mass.

16. A method of high-frequency ablation employing a device having:
an electrical probe adapted for percutaneous insertion into tissue to a tumor site;
a high-frequency power source communicating with the electrical probe to ablate tissue at the tumor site;
an actuator communicating with the electrode to provide vibration of the electrode along a first axis;
a tissue imager measuring axial displacement of tissue in a volume extending from the tumor site along a second axis perpendicular to the first axis, such displacement characterizing a shear wave directed along the second axis; and
an electronic computer receiving displacement data from the tissue imager and executing a stored program to:
(a) computing a velocity of a shear wave along the second axis;
(b) detect a change in shear wave velocity along the second axis indicating a boundary between ablated and non-ablated tissue along the second axis; and
(c) output data indicating a size of an ablation region along the second axis,
the method comprising the steps of:
(a) computing a velocity of a shear wave along the second axis;
(b) detecting a change in shear wave velocity along the second axis indicating a boundary between ablated and non-ablated tissue along the second axis; and
(c) outputting data indicating a size of an ablation region along the second axis based on the detected change in shear wave velocity.

* * * * *